(12) United States Patent  (10) Patent No.: US 7,994,207 B2
Zierke et al.  (45) Date of Patent: Aug. 9, 2011

(54) PROCESS FOR PREPARING FLUOROMETHYL-SUBSTITUTED HETEROCYCLIC COMPOUNDS

(75) Inventors: Thomas Zierke, Böhl-Iggelheim (DE); Michael Rack, Eppelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/519,032

(22) PCT Filed: Dec. 20, 2007

(86) PCT No.: PCT/EP2007/064390
§ 371 (c)(1),
(2), (4) Date: Jun. 12, 2009

(87) PCT Pub. No.: WO2008/077907
PCT Pub. Date: Jul. 3, 2008

(65) Prior Publication Data
US 2010/0022782 A1    Jan. 28, 2010

(30) Foreign Application Priority Data
Dec. 21, 2006 (EP) .................................... 06126937

(51) Int. Cl.
*A61K 31/415* (2006.01)
*C07D 231/12* (2006.01)
(52) U.S. Cl. ..................................... 514/403; 548/374.1
(58) Field of Classification Search ............... 548/374.1; 514/403
See application file for complete search history.

(56) References Cited

U.S. PATENT DOCUMENTS

| 5,618,951 | A | 4/1997 | Britton |
| 2006/0276656 | A1 | 12/2006 | Lantzsch et al. |
| 2008/0015244 | A1 | 1/2008 | Dunkel et al. |
| 2008/0108686 | A1 | 5/2008 | Gewehr et al. |
| 2010/0069646 | A1 | 3/2010 | Sukopp et al. |

FOREIGN PATENT DOCUMENTS

| WO | WO 92/12970 | 8/1992 |
| WO | WO 93/11117 | 6/1993 |
| WO | WO 2005/044804 | 8/2003 |
| WO | WO 03/070705 | 5/2005 |
| WO | WO-2005/044804 | * 5/2005 |
| WO | WO 2005/123690 | 12/2005 |
| WO | WO 2007/031323 | 3/2007 |
| WO | WO 2008/053043 | 5/2008 |

OTHER PUBLICATIONS

International Search Report for International Application No. PCT/EP2006/008982; International Filing Date: Dec. 20, 2007; Date of Completion: Dec. 11, 2006; Date of mailing: Dec. 19, 2006.
International Preliminary Report on Patentability for International Application No. PCT/EP2006/008982; International Filing Date: Dec. 20, 2007; Date of Issuance: Jul. 7, 2009.
International Search Report for International Application No. PCT/EP2007/064390.

* cited by examiner

*Primary Examiner* — Joseph K. McKane
*Assistant Examiner* — Janet L Coppins
(74) *Attorney, Agent, or Firm* — Brinks Hofer Gilson & Lione

(57) ABSTRACT

The present invention relates to a process for preparing fluoromethyl-substituted heterocyclic compounds of the general formula (I)

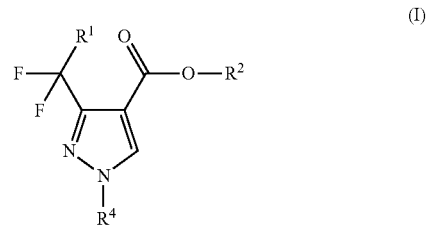

in which $R^1$ is H or F; $R^2$ is an $-[A-O]_m-R^3$ group in which A is $C_2-C_4$-alkanediyl, $R^3$ is $C_1-C_4$-alkyl and m is 1 or 2;
by converting the corresponding chloromethyl-substituted compounds (II) in the presence of fluorinating agents,
to processes for preparing the chloromethyl-substituted compounds (II),
to processes for preparing amides of the general formula (IV)

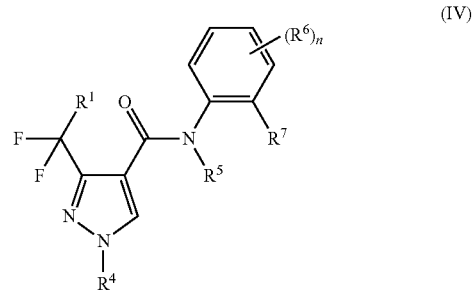

and to compounds of the general formulae (I) and (II).

13 Claims, No Drawings

PROCESS FOR PREPARING FLUOROMETHYL-SUBSTITUTED HETEROCYCLIC COMPOUNDS

This application is a National Stage application of International Application No. PCT/EP2007/064390 filed Dec. 20, 2007, the entire contents of which is hereby incorporated herein by reference. This application also claims the benefit under 35 U.S.C. §119 of European Patent Application No. 06126937.9, filed Dec. 21, 2006, the entire contents of which is hereby incorporated herein by reference.

The present invention relates to a process for preparing fluoromethyl-substituted heterocyclic compounds by converting the corresponding chloromethyl-substituted compounds in the presence of fluorinating agents.

WO 2005/044804 describes lower alkyl esters of fluoromethyl-substituted heterocyclic carboxylic acids and their preparation by fluorinating the corresponding chloromethyl-substituted heterocyclic carboxylic esters and their further processing to the anilides of the fluoromethyl-substituted heterocyclic carboxylic acids. The process is unsatisfactory in several respects.

It is thus an object of the present invention to provide further fluoromethyl-substituted heterocyclic compounds, especially 3-difluoromethylpyrazol-4-yl- or 3-trifluoromethylpyrazol-4-ylcarboxylic esters, and processes for preparing these compounds. These fluoromethyl-substituted pyrazol-4-ylcarboxylic esters shall feature improved convertibility to the corresponding amides. Moreover, the provision of the starting compounds for the preparation of the fluoromethyl-substituted pyrazol-4-ylcarboxylic esters with improved selectivity with regard to the N-substitution shall be enabled.

It has been found that, surprisingly, the heterocyclic carboxylic esters of the formulae I and II described hereinafter achieve these objects and therefore are advantageously suitable for preparing anilides of fluoromethyl-substituted heterocyclic carboxylic acids.

The present invention therefore provides fluoromethyl-substituted heterocyclic compounds of the general formula (I)

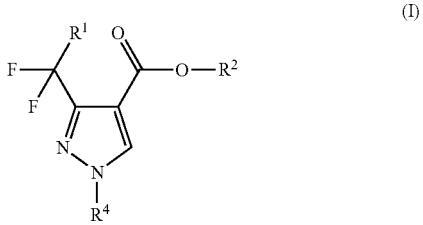

(I)

in which
R$^1$ is hydrogen or fluorine;
R$^2$ is an -[A-O]$_m$—R$^3$ group in which
  A is C$_2$-C$_4$-alkanediyl,
  R$^3$ is C$_1$-C$_4$-alkyl and
  m is 1 or 2;
R$^4$ is selected from C$_1$-C$_6$-alkyl, C$_1$-C$_6$-haloalkyl, C$_3$-C$_6$-cycloalkyl, C$_1$-C$_4$-alkoxy-C$_1$-C$_4$-alkyl, C$_1$-C$_4$-alkylthio-C$_1$-C$_4$-alkyl, C$_1$-C$_4$-haloalkoxy-C$_1$-C$_4$-alkyl, C$_1$-C$_6$-alkylcarbonyl, C$_1$-C$_6$-alkoxycarbonyl, phenyl and benzyl, where the latter two radicals may optionally be substituted by any combination of 1, 2 or 3 R$^{3'4}$ radicals selected independently from halogen, cyano, nitro, C$_1$-C$_4$-alkyl, C$_1$-C$_4$-haloalkyl, C$_1$-C$_4$-alkoxy and C$_1$-C$_4$-haloalkoxy;
and a process for their preparation, wherein a chloromethyl-substituted heterocyclic compound of the general formula (II)

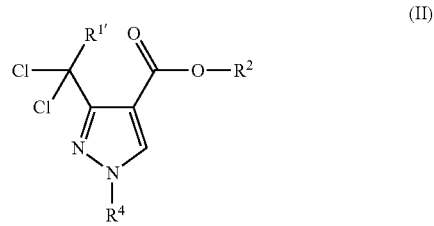

(II)

in which R$^{1'}$ is hydrogen or chlorine and R$^2$ and R$^4$ are each as defined above is converted in the presence of a fluorinating agent.

The inventive compounds of the formula (I) can be prepared in high yields, selectivities and purities. A further advantage is the high selectivity based on the position of the R$^4$ radical, since even the precursor of the formula (II) can be prepared with high regioselectivity. In addition, the process according to the invention allows the use of inexpensive starting materials. A further advantage is the fact that both the workup of the reaction mixtures obtained in the fluorination and the further conversion of the compounds of the formula (I) to carboxamides can be performed without any problem.

The terms for organic groups used in the definition of the variables are, for example the expression "halogen", collective terms which represent the individual members of these groups of organic units. In the particular case, the prefix C$_x$-C$_y$ denotes the number of possible carbon atoms.

The term "halogen" in each case denotes fluorine, bromine, chlorine or iodine, especially fluorine, chlorine or bromine.

Examples of other definitions are:

The term "C$_1$-C$_6$-alkyl", as used herein and in the terms C$_1$-C$_6$-alkoxy, C$_1$-C$_6$-alkyl-amino, di(C$_1$-C$_6$-alkyl)amino, C$_1$-C$_6$-alkylthio, C$_1$-C$_6$-alkylsulfonyl, C$_1$-C$_6$-alkylsulfoxyl, C$_1$-C$_6$-alkylcarbonyl, C$_1$-C$_6$-alkoxycarbonyl, and C$_1$-C$_6$-alkylcarbonyloxy, denotes a saturated, straight-chain or branched hydrocarbon group comprising from 1 to 6 carbon atoms, especially from 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethyl-butyl, 2,3-dimethylbutyl, 3,3-dimethylbutyl, 1-ethylbutyl, 2-ethylbutyl, 1,1,2-trimethyl-propyl, 1,2,2-trimethylpropyl, 1-ethyl-1-methylpropyl, 1-ethyl-2-methylpropyl and isomers thereof. C$_1$-C$_4$-Alkyl comprises, for example, methyl, ethyl, propyl, 1-methyl-ethyl, butyl, 1-methylpropyl, 2-methylpropyl or 1,1-dimethylethyl.

The term "C$_1$-C$_6$-haloalkyl", as used herein and in the haloalkyl units of C$_1$-C$_6$-halo-alkoxy, C$_1$-C$_6$-haloalkoxy-C$_1$-C$_6$-alkyl and haloalkylthio, describes straight-chain or branched alkyl groups having from 1 to 6 carbon atoms, where some or all of the hydrogen atoms of these groups are replaced by halogen atoms, for example C$_1$-C$_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, etc.

The term "$C_1$-$C_6$-alkoxy" as used herein describes straight-chain or branched saturated alkyl groups which comprise from 1 to 6 carbon atoms and are bonded via an oxygen atom. Examples comprise $C_1$-$C_6$-alkoxy, for example methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethyl-butoxy, 1,3-dimethylbutoxy, 2,2-dimethylbutoxy, 2,3-dimethylbutoxy, 3,3-dimethyl-butoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, etc.

The term "$C_1$-$C_6$-haloalkoxy" as used herein describes $C_1$-$C_6$-alkoxy groups as described above, wherein some or all of the hydrogen atoms of these groups are replaced by halogen atoms, i.e., for example, $C_1$-$C_6$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoro-propoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, especially chloromethoxy, fluoromethoxy, difluoromethoxy, trifluoromethoxy, 2-fluoroethoxy, 2-chloroethoxy or 2,2,2-trifluoroethoxy.

The term "$C_1$-$C_4$-alkoxy-$C_1$-$C_4$-alkyl" as used herein describes a $C_1$-$C_4$-alkyl radical in which one hydrogen atom has been replaced by a $C_1$-$C_4$-alkoxy radical. Examples thereof are $CH_2$—$OCH_3$, $CH_2$—$OC_2H_5$, n-propoxymethyl, $CH_2$—$OCH(CH_3)_2$, n-butoxy-methyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methyl-ethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methyl-propoxy)propyl, 3-(2-methylpropoxy)propyl, 3-(1,1-dimethylethoxy)propyl, 2-(methoxy)-butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)-butyl, 4-(n-butoxy)butyl, 4-(1-methylpropoxy)butyl, 4-(2-methylpropoxy)butyl, 4-(1,1-dimethylethoxy)butyl, etc.

The term "$C_1$-$C_6$-alkylcarbonyl" as used herein describes a straight-chain or branched saturated alkyl group which comprises from 1 to 6 carbon atoms and is bonded terminally or internally via the carbon atom of a carbonyl unit. Examples comprise $C_1$-$C_6$-alkylcarbonyls such as $C(O)$—$CH_3$, $C(O)$—$C_2H_5$, n-propylcarbonyl, 1-methylethylcarbonyl, n-butylcarbonyl, 1-methylpropylcarbonyl, 2-methylpropyl-carbonyl, 1,1-dimethylethylcarbonyl, n-pentylcarbonyl, 1-methylbutylcarbonyl, 2-methyl-butylcarbonyl, 3-methylbutylcarbonyl, 1,1-dimethylpropylcarbonyl, 1,2-dimethyl-propylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methyl-pentylcarbonyl, 1,1-dimethylbutylcarbonyl, 1,2-dimethylbutylcarbonyl, 1,3-dimethyl-butylcarbonyl, 2,2-dimethylbutylcarbonyl, 2,3-dimethylbutylcarbonyl, 3,3-dimethylbutyl-carbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methyl-propylcarbonyl, etc.

The term "$C_1$-$C_6$-alkoxycarbonyl" as used herein describes a straight-chain or branched alkoxy group which comprises from 1 to 6 carbon atoms and is bonded via the carbon atom of a carbonyl unit. Examples comprise ($C_1$-$C_6$-alkoxy)carbonyls such as $C(O)$—$OCH_3$, $C(O)$—$OC_2H_5$, $C(O)$—$O$—$CH_2$—$C_2H_5$, $C(O)$—$OCH(CH_3)_2$, n-butoxycarbonyl, $C(O)$—$OCH(CH_3)$—$C_2H_5$, $C(O)$—$OCH_2CH(CH_3)_2$, $C(O)$—$OC(CH_3)_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethyl-propoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethyl-butoxycarbonyl, 1,2-dimethylbutoxycarbonyl, 1,3-dimethylbutoxycarbonyl, 2,2-dimethyl-butoxycarbonyl, 2,3-dimethylbutoxycarbonyl, 3,3-dimethylbutoxycarbonyl, 1-ethyl-butoxycarbonyl, 2-ethylbutoxycarbonyl, 1,1,2-trimethylpropoxycarbonyl, 1,2,2-trimethyl-propoxycarbonyl, 1-ethyl-1-methylpropoxycarbonyl or 1-ethyl-2-methylpropoxycarbonyl, etc.

The term "$C_1$-$C_6$-alkylcarbonyloxy" as used herein describes straight-chain or branched saturated alkyl groups which comprise from 1 to 6 carbon atoms and are bonded terminally or internally via the carbon atom of the carbonyloxy unit. Examples comprise $C_1$-$C_6$-alkylcarbonyloxy such as $O$—$C(O)$—$CH_3$, $O$—$C(O)$—$C_2H_5$, n-propylcarbonyloxy, 1-methylethylcarbonyloxy, n-butylcarbonyloxy, 1-methylpropylcarbonyloxy, 2-methyl-propylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropyl-carbonyloxy, 1,2-dimethylpropylcarbonyloxy, etc.

The term "$C_2$-$C_6$-alkenyl" as used herein and for the alkenyl units of $C_2$-$C_6$-alkenyloxy describes straight-chain and branched unsaturated hydrocarbon radicals comprising from 2 to 6 carbon atoms and at least one carbon-carbon double bond, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_6$-alkenyloxy" as used herein describes straight-chain or branched alkenyl groups which comprise from 2 to 6 carbon atoms and are bonded via an oxygen atom, for example vinyloxy, allyloxy (propen-3-yloxy), methallyloxy, buten-4-yloxy, etc.

The term "$C_2$-$C_6$-alkynyl", as used herein and in the alkynyl units of $C_2$-$C_6$-alkynyloxy, $C_2$-$C_6$-alkynylamino, $C_2$-$C_6$-alkynylthio, $C_2$-$C_6$-alkynylsulfonyl, $C_2$-$C_6$-alkynylcarbonyl, $C_2$-$C_6$-alkynyloxycarbonyl and $C_1$-$C_6$-alkynylcarbonyloxy, describes straight-chain and branched unsaturated hydrocarbons comprising from 2 to 6 carbon atoms and at least one carbon-carbon triple bond, for example ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and others.

The term "$C_3$-$C_8$-cycloalkyl" as used herein describes mono-, bi- or polycyclic hydrocarbon radicals comprising from 3 to 8 carbon atoms, especially from 3 to 6 carbon atoms. Examples of monocyclic radicals comprise cyclopropyl, cyclobutyl, cyclopentyl, cyclohexyl, cycloheptyl or cyclooctyl. Examples of bicyclic radicals comprise bicyclo[2.2.1]heptyl, bicyclo[3.1.1]heptyl, bicyclo[2.2.2]octyl and bicyclo[3.2.1]octyl. Examples of tricyclic radicals are adamantyl and homoadamantyl.

Each cycloalkyl radical may optionally be substituted by 1, 2, 3, 4 or 5 of the aforementioned R# radicals. In other words, 1, 2, 3, 4 or 5 of the hydrogen atoms of these radicals may each independently be replaced by the aforementioned R# radicals. The substituents R# of cycloalkyl radicals are preferably selected from halogen, especially fluorine or chlorine, or $C_1$-$C_6$-alkyl.

The term "($C_2$-$C_4$)-alkanediyl" as used herein describes ethane-1,2-diyl, propane-1,3-diyl and butane-1,4-diyl.

In a specific embodiment of the invention, $R^1$ in the general formula (I) and $R^{1'}$ in the general formula (II) are each hydrogen.

In the compounds of the formulae (I) and (II), m is preferably 1.

Examples of suitable $R^2$ radicals in which m is 1 are 2-methoxyethyl, 3-methoxypropyl, 4-methoxybutyl, 2-ethoxyethyl, 3-ethoxypropyl, 4-ethoxybutyl, 2-(propoxy)ethyl, 3-(propoxy)propyl, 4-(propoxy)butyl, 2-(1-methylethoxy)ethyl, 3-(1-methylethoxy)propyl, 4-(1-methylethoxy)butyl, 2-(butoxy)ethyl, 3-(butoxy)propyl, 4-(butoxy)butyl, 2-(2-methylpropoxy)ethyl, 3-(2-methylpropoxy)propyl, 4-(2-methylpropoxy)butyl, 2-(1,2-dimethylethoxy)ethyl, 3-(1,2-dimethylethoxy)propyl and 4-(1,2-dimethylethoxy)butyl, preferably 2-methoxyethyl, 3-methoxypropyl, 2-ethoxyethyl or 3-ethoxypropyl and more preferably 2-methoxyethyl or 2-ethoxyethyl stands.

$R^4$ is preferably selected from hydrogen, $C_1$-$C_6$-alkyl, $C_3$-$C_6$-cycloalkyl and optionally substituted phenyl, especially from hydrogen and $C_1$-$C_4$-alkyl. $R^4$ is more preferably $C_1$-$C_4$-alkyl; $R^4$ is especially methyl.

Suitable fluorinating agents for converting chloromethyl-substituted heterocyclic compounds of the general formula (II) in the presence of a fluorinating agent (referred to hereinafter as halogen exchange reaction) are in principle all fluorinating agents used customarily for halogen exchange reactions. However, the fluorinating agent is preferably selected from alkali metal fluorides such as sodium fluoride, potassium fluoride or caesium fluoride, cobalt (III) fluoride, antimony fluoride, molybdenum fluoride, hydrogen fluoride, hydrogen fluoride/pyridine mixtures, tertiary ammonium hydrofluorides or trialkylamine hydrofluorides of the general formula n*HF/N($C_1$-$C_4$-alkyl)$_3$, where n is 1, 2 or 3. The fluorinating agent is more preferably selected from triethylamine tris-hydrofluoride, tri-n-butylamine tris-hydrofluoride and hydrogen fluoride/pyridine mixtures, especially from triethylamine tris-hydrofluoride and tri-n-butylamine tris-hydrofluoride.

The fluorinating agent is used in a molar ratio of fluoride equivalents per chlorine atom to be replaced in the range from 1:1 to 3:1. The fluorinating agent is preferably used in a molar ratio in the range from 1:1 to 1.5:1.

The halogen exchange reaction takes place preferably at a temperature in the range from 80 to 170° C., especially at a temperature in the range from 100 to 150° C.

The halogen exchange reaction can be effected at standard pressure or in an autoclave under autogenous pressure. The pressure is preferably within a range of from 0.1 to 50 bar, especially in the range from 1 to 10 bar.

In addition to the halogen exchange reaction, the invention further relates to the provision of the compound of the general formula (II).

Compounds of the general formula (II) can be prepared in analogy to synthesis routes to the preparation of similar chloromethyl-substituted heterocycles, some of which are known (WO 92/12970, WO 93/11117, WO 2005/044804).

A particularly suitable synthesis route to the provision of compounds of the general formula (II) is shown below by way of example.

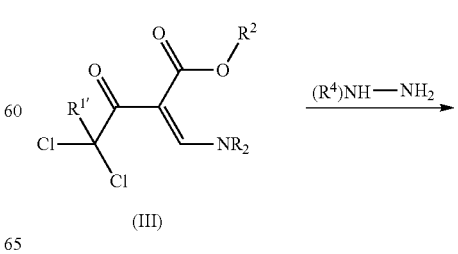

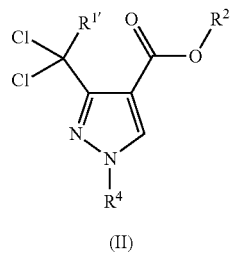

(II)

Pyrazole compounds of the general formula (II) are obtainable by reaction of 2-acyl-N,N-dialkyl-3-aminoacrylic esters (III) with hydrazine or suitable hydrazine derivatives. In this reaction, hydrazine or the hydrazine derivative is typically used in an about equimolar amount, for example in a molar ratio of (III):(hydrazine or hydrazine derivative) in the range from 0.8:1 to 1:1.2. In general, the reaction is effected in a dry inert solvent, for example aromatic hydrocarbons, e.g. toluene, xylenes, etc. The reaction is effected generally under protective gas atmosphere, for example under nitrogen. In general, hydrazine or the hydrazine derivative will be initially charged, and a solution of the 3-aminoacrylic ester in an inert solvent which has been dried if appropriate will be added with cooling. The product is subsequently isolated, if necessary, by suitable separation processes, for example extraction, crystallization and/or column chromatography.

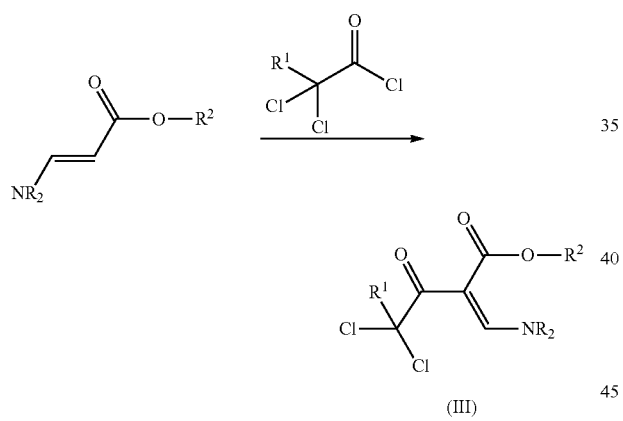

(III)

2-Acyl-N,N-dialkyl-3-aminoacrylic esters (III) can be provided, for example, by reacting 3-N,N-dialkylaminoacrylic esters with halogenated acetyl chlorides. Typically, the reaction is effected in an inert solvent, for example toluene. The molar ratio of diethylaminoacrylic ester to the halogenated acetyl chloride is typically in the range from 0.8:1 to 1:1.2 and is especially about equimolar. For the reaction, the dialkylaminoacrylic ester will typically be initially charged in an inert solvent and the halogenated acetyl chloride will be added slowly thereto with cooling as a solution. The product of the reaction is then isolated by customary separation processes as specified above.

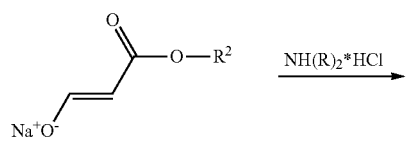 NH(R)$_2$*HCl

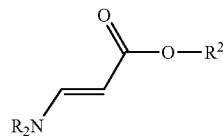

3-N,N-Dimethylaminoacrylic esters in turn can be provided from the alkali metal salts of formylacetic esters, especially from the sodium salts, by reaction with hydrochlorides of secondary amines, especially dimethylamine hydrochloride. Typically, the hydro-chloride of the secondary amine will be initially charged in an inert nonpolar solvent and a solution of the salt of the formylacetic ester will be added slowly. The molar ratio of (alkali metal salt of the formylacetic ester):(hydrochloride of the secondary amine) is generally in the range from 0.8:1.2 to 1:1.2; the two compounds are especially used in about equimolar amounts. When the salt formed as the by-product precipitates out under the specific reaction conditions, it can be removed after the reaction has ended by a suitable method, for example filtration, and the filtrate comprising the desired reaction product is freed of volatile constituents, for example by evaporation. The reaction product is, if necessary, isolated from the residue by suitable separating methods.

The present invention therefore further relates to processes for preparing compounds of the general formula (II), wherein a compound of the general formula (III) in which $R^{1'}$ and $R^2$ each have the definition given above is converted in the presence of hydrazine or of a hydrazine derivative of the formula $(C_1\text{-}C_4\text{-alkyl})NH\text{—}NH_2$. In particular, methylhydrazine is used for this purpose.

The inventive compounds of the general formula (I) are advantageously suitable for synthesizing a multitude of compounds which are of interest as active ingredients, for example fungicidal carboxamides.

The invention therefore further relates to a process for preparing amides of the general formula (IV)

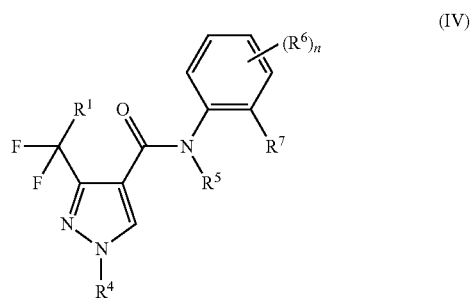

(IV)

in which
$R^1$ and $R^4$ each have the definition given above;
$R^5$ is selected from $C_1$-$C_6$-alkyl, $C_1$-$C_6$-haloalkyl, $C_3$-$C_8$-cycloalkyl, $C_3$-$C_8$-halocycloalkyl, $C_1$-$C_4$-alkoxy-$C_1$-$C_4$-alkyl, $C_1$-$C_4$-haloalkoxy-$C_1$-$C_4$-alkyl;
$R^6$ is selected from hydrogen, halogen, $C_1$-$C_6$-alkyl, $C_1$-$C_6$-alkoxy, $C_1$-$C_6$-alkylthio, $C_1$-$C_6$-haloalkyl, $C_1$-$C_6$-haloalkoxy or $C_1$-$C_6$-haloalkylthio;
n is 1, 2, 3 or 4;
$R^7$ is selected from $C_1$-$C_{20}$-alkyl, $C_2$-$C_{20}$-alkenyl, $C_2$-$C_{20}$-alkynyl, which may optionally be substituted by a combination of Ray radicals, where $R^{ay}$ are each independently selected from halogen, cyano, nitro, hydroxyl, mercapto, amino, carboxyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy and $C_1$-$C_6$-alkylcarbonyloxy;

$C_3$-$C_8$-cycloalkyl, $C_4$-$C_{14}$-bicycloalkyl and phenyl which may optionally be substituted by a combination of 1, 2, 3, 4 or 5 $R^{ax}$ radicals, where $R^{ax}$ are each independently selected from halogen, cyano, nitro, hydroxyl, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-halo-alkoxy, $C_1$-$C_6$-alkylthio, $C_1$-$C_6$-alkylamino, di($C_1$-$C_6$-alkyl)amino, $C_1$-$C_6$-alkyl-sulfonyl, $C_1$-$C_6$-alkylsulfoxyl, formyl, $C_1$-$C_6$-alkylcarbonyl, $C_1$-$C_6$-alkoxy-carbonyl, formyloxy and $C_1$-$C_6$-alkylcarbonyloxy; and wherein at least one fluoromethyl-substituted heterocyclic compound of the general formula (I) is subjected to a chemical conversion of the carboxyl group to an amide function.

Suitable methods of converting esters to amides are known to those skilled in the art. For example, the ester function of the compounds of the general formula (I) can be converted by hydrolysis to the free carboxylic acid or to the corresponding carboxylate anion in the presence of an acid or base, preferably in the presence of a base. The carboxylic acid can subsequently be reacted under suitable reaction conditions with a corresponding aniline derivative directly to give a compound of the general formula (IV), or can, if appropriate, be converted to a more reactive species before the reaction with the aniline derivative, for example to an acid chloride. Depending on the synthesis route selected, the coupling reaction of carboxylic acid derivative and aniline derivative can, if appropriate, be performed in the presence of catalysts, condensation agents, acid binding agents and/or with separation of water, for example by azeotropic distillation. The methods for this purpose and for isolating the desired product of the general formula (IV) are known to those skilled in the art.

The preparation of fluoromethyl-substituted heterocyclic compounds will be illustrated hereinafter with reference to examples. These examples fulfill a purely illustrative purpose and should not be interpreted in a restrictive manner.

EXAMPLE 1

Preparation of 2-methoxyethyl 3-difluoromethyl-1-methyl-1H-pyrazol-4-yl-carboxylate 1.1 2-Methoxyethyl 3-N, N-dimethylaminoacrylate To a suspension of sodium hydride (12.0 g, 0.30 mol) in dry toluene (100 ml) was added dropwise 2-methoxyethanol (22.8 g, 0.30 mol) at a rate such that the temperature did not significantly exceed 30° C. (about 30 min). After the gas evolution had ended, the reaction solution was stirred at room temperature for a further 3 h. The reaction solution was admixed with dry toluene (20 ml) and 2-methoxyethyl acetate (47.9 g, 0.40 mol) and transferred to an autoclave. The autoclave was heated to 60° C. at a CO pressure of 20 bar for 12 h. After cooling and decompression, the reaction mixture was admixed again with toluene (20 ml) and added dropwise to dimethylamine hydrochloride (24.8 g, 0.30 mol) in toluene (100 ml) over a period of 30 min. The reaction mixture was stirred for a further 3 h, the precipitated crystalline solid was removed by filtration and the filtrate was freed from the solvent under reduced pressure. The desired reaction product was obtained after fractional distillation.

$^1$H-NMR (400 MHz, $CDCl_3$): δ=2.6-3.1 (s broad, 6H), 3.4 (d, 3H), 3.62 (t, 2H), 4.22 (t, 2H), 4.57 (d, 1H), 7.47 ppm (d, 1H).

1.2 2-Methoxyethyl 4,4-dichloro-2-(N, N-dimethylaminomethylene)acetoacetate

2-Methoxyethyl 3-N,N-dimethylaminoacrylate (14 g, 0.08 mol) was initially charged in toluene (200 ml) and cooled to a temperature of from 0 to 5° C. A solution of dichloroacetyl chloride (12.0 g, 0.08 mol) in toluene (20 ml) was added dropwise over a period of 20 min. Subsequently, an aqueous solution of NaOH (10%, 0.08 mol) was slowly added dropwise to the reaction solution at a temperature of from 0 to 5° C. After stirring at this temperature for three hours, the mixture was warmed to room temperature. After the phases had been separated, the aqueous phase was extracted with toluene (50 ml). The combined organic phases were washed with water (50 ml) and freed of the volatile constituents on a rotary evaporator. 23 g of 2-methoxyethyl 4,4-dichloro-2-(N, N-dimethylamino-methylene)acetoacetate were obtained.

1.3 2-Methoxyethyl 3-dichloromethyl-1-methyl-1H-pyrazole-4-carboxylate

Methylhydrazine (3.8 g, 0.08 mol) were initially charged in dry toluene (90 ml) under nitrogen and cooled to approx. 0° C. At this temperature, a solution of 2-methoxyethyl 4,4-dichloro-2-(N,N-dimethylaminomethylene)acetoacetate (23 g, 0.08 mol) in dry toluene (90 ml) was slowly added dropwise over a period of a ½ hour. After the addition had ended, the mixture was stirred at 0° C. for a further 3 hours and then warmed to room temperature. After the reaction had ended, the reaction solution was washed with water (100 ml). The washing phase was extracted with toluene (100 ml); the two organic phases were combined and freed of the volatile constituents under reduced pressure. The residue was purified by column chromatography ($SiO_2$, ethyl acetate:petroleum ether, 1:1) and analyzed by means of GC monitoring and $^1$H NMR. The desired product was obtained with a yield of 7.7 g (0.03 mol) in a purity of 95.5 area %.

CI-MS: m/e=267 ($M^+$); $^1$H NMR (500 MHz, $CDCl_3$): δ=3.4 (s, 3H), 3.67 (t, 2H), 3.95 (s, 3H), 4.4 (t, 2H), 7.4 (s, 1H), 7.9 ppm (s, 1H); $^{13}$C NMR (127 MHz, $CDCl_3$): δ=39.82 ($CH_3$), 58.93 ($CH_3$), 62.59 (CH), 63.51 ($CH_2$), 70.39 ($CH_2$), 110.19 (quart. C), 134.87 (CH), 151.39 (quart. C), 161.79 ppm (quart. C).

1.4 2-Methoxyethyl 3-difluoromethyl-1-methyl-1H-pyrazol-4-yl-carboxylate

2-Methoxyethyl 3-dichloromethyl-1-methyl-1H-pyrazole-4-carboxylate and triethylamine tris-hydrofluoride were heated at 145° C. under autogenous pressure (<1 bar) in an autoclave for 10 h. After cooling to room temperature, the reaction mixture was dissolved in dichloromethane, washed with water and a saturated aqueous NaCl solution, dried over $MgSO_4$ and freed of the volatile constituents under reduced pressure. The desired product was obtained with a yield of 2.7 g (0.01 mol, 88% of theory). The purity was determined by $^1$H NMR and was about 90%.

$^1$H NMR (500 MHz, CDCl$_3$): δ=3.4 (s, 3H), 3.65 (t, 2H), 3.97 (s, 3H), 4.4 (t, 2H), 7.12 (t, 1H, $^{19}$F $^2$J coupling=74 Hz), 7.95 ppm (s, 1H).

The invention claimed is:

1. A process for preparing fluoromethyl-substituted heterocyclic compounds of formula (I)

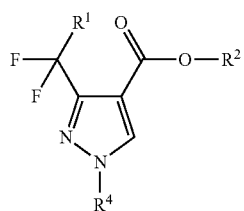

(I)

wherein
R$^1$ is hydrogen or fluorine;
R$^2$ is an -[A-O]$_m$—R$^3$ group in which
A is C$_2$-C$_4$-alkanediyl,
R$^3$ is C$_1$-C$_4$-alkyl and
m is 1 or 2;
R$^4$ is selected from the group consisting of hydrogen, C$_1$-C$_6$-alkyl, C$_1$-C$_6$-haloalkyl, C$_3$-C$_6$-cycloalkyl, C$_1$-C$_4$-alkoxy-C$_1$-C$_4$-alkyl, C$_1$-C$_4$-alkylthio-C$_1$-C$_4$-alkyl, C$_1$-C$_4$-haloalkoxy-C$_1$-C$_4$-alkyl, C$_1$-C$_6$-alkylcarbonyl, C$_1$-C$_6$-alkoxycarbonyl, phenyl and benzyl, wherein the latter two radicals may optionally be substituted by any combination of 1, 2 or 3 R$^{3'4}$ radicals selected independently from the group consisting of halogen, cyano, nitro, C$_1$-C$_4$-alkyl, C$_1$-C$_4$-haloalkyl, C$_1$-C$_4$-alkoxy and C$_1$-C$_4$-haloalkoxy; and
wherein a chloromethyl-substituted heterocyclic compound of the general formula (II)

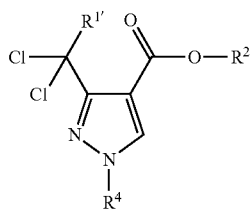

(II)

in which R$^{1'}$ is hydrogen or chlorine and R$^2$ and R$^4$ are each as defined above is subjected to conversion in the presence of a fluorinating agent wherein fluoromethyl-substituted heterocyclic compounds are prepared.

2. The process of claim 1, wherein R$^1$ in formula (I) and R$^{1'}$ in formula (II) are each hydrogen.

3. The process of claim 1, wherein m is 1.

4. The process of claim 3, wherein R$^2$ is 2-methoxyethyl, 3-methoxypropyl, 2-ethoxyethyl or 3-ethoxypropyl.

5. The process of claim 4, wherein R$^2$ is 2-methoxyethyl or 2-ethoxyethyl.

6. The process of claim 1, wherein R$^4$ is hydrogen or C$_1$-C$_4$-alkyl.

7. The process of claim 6, wherein R$^4$ is C$_1$-C$_4$-alkyl.

8. The process of claim 1, wherein said fluorinating agent is selected from the group consisting of alkali metal fluorides, cobalt(III) fluoride, antimony fluoride, molybdenum fluoride, hydrogen fluoride, hydrogen fluoride/pyridine mixtures, tertiary ammonium hydrofluorides or trialkylamine hydrofluorides of formula n*HF/N(C$_1$-C$_4$-alkyl)$_3$, where n is 1, 2 or 3.

9. The process of claim 8, wherein said fluorinating agent is selected from the group consisting of triethylamine tris-hydrofluoride, tri-n-butylamine tris-hydrofluoride and hydrogen fluoride/pyridine mixtures.

10. The process of claim 9, wherein said fluorinating agent is selected from the group consisting of triethylamine tris-hydrofluoride and tri-n-butylamine tris-hydrofluoride.

11. The process of claim 1, wherein said compounds of formula (II) are subjected to said conversion at a temperature of from 80 to 170° C.

12. A process for preparing compounds of formula (II),

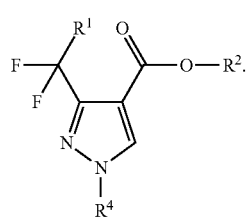

(I)

wherein a compound of formula (III)

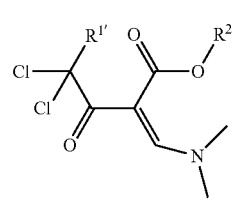

(III)

wherein
R$^{1'}$ is hydrogen or fluorine;
R$^2$ is an -[A-O]$_m$—R$^3$ group in which
A is C$_2$-C$_4$-alkanediyl,
R$^3$ is C$_1$-C$_4$-alkyl,
m is 1 or 2; and
R$^4$ is C$_1$-C$_4$-alkyl;
is subjected to conversion in the presence of hydrazine or of a hydrazine derivative of the formula (C$_1$-C$_4$-alkyl)NH—NH$_2$.

13. A process for preparing amides of formula (IV)

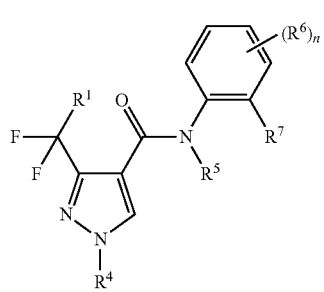

(IV)

wherein
R$^1$ is hydrogen or fluorine;

$R^4$ is selected from the group consisting of hydrogen, $C_1$-$C_6$-alkyl, $C_3$-$C_6$-cycloalkyl, $C_1$-$C_4$-alkoxy-$C_1$-$C_4$-alkyl, $C_1$-$C_4$-haloalkoxy-$C_1$-$C_4$-alkyl, $C_1$-$C_6$-alkylcarbonyl, $C_1$-$C_6$-alkoxycarbonyl, phenyl and benzyl, wherein the latter two radicals may optionally be substituted by any combination of 1, 2 or 3 $R^{y4}$ radicals selected independently from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^5$ is selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_1$-$C_4$-alkoxy-$C_1$-$C_4$-alkyl and $C_1$-$C_4$-haloalkoxy-$C_1$-$C_4$-alkyl;

$R^6$ is selected from the group consisting of hydrogen, halogen, $C_1$-$C_6$-alkyl, $C_1$-$C_6$-alkoxy, $C_1$-$C_6$-alkylthio, $C_1$-$C_6$-haloalkyl, $C_1$-$C_6$-haloalkoxy and $C_1$-$C_6$-haloalkylthio;

n is 1, 2, 3 or 4;

$R^7$ is selected from the group consisting of $C_1$-$C_{20}$-alkyl, $C_2$-$C_{20}$-alkenyl, $C_2$-$C_{20}$-alkynyl, which may optionally be substituted by a combination of $R^{ay}$ radicals, where $R^{ay}$ are each independently selected from the group consisting of halogen, cyano, nitro, hydroxyl, mercapto, amino, carboxyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl) amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy and $C_1$-$C_6$-alkylcarbonyloxy;

$C_3$-$C_8$-cycloalkyl, $C_4$-$C_{14}$-bicycloalkyl, phenyl which may optionally be substituted by a combination of 1, 2, 3, 4 or 5 $R^{ax}$ radicals, where $R^{ax}$ are each independently selected from the group consisting of halogen, cyano, nitro, hydroxyl, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl) amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy and $C_1$-$C_6$-alkylcarbonyloxy; and wherein at least one fluoromethyl-substituted heterocyclic compound of formula (I)

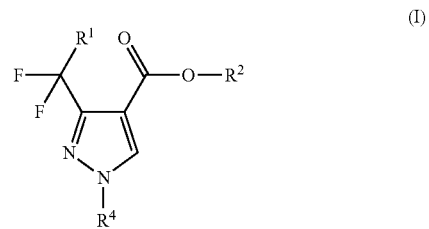

(I)

wherein $R^1$ and $R^4$ are as described above and
$R^2$ is an -[A-O]$_m$—$R^3$ group in which
A is $C_2$-$C_4$-alkanediyl,
$R^3$ is $C_1$-$C_4$-alkyl and
m is 1 or 2;

is subjected to conversion of the carboxyl group to an amide function.

* * * * *

UNITED STATES PATENT AND TRADEMARK OFFICE
CERTIFICATE OF CORRECTION

| | |
|---|---|
| PATENT NO. | : 7,994,207 B2 |
| APPLICATION NO. | : 12/519032 |
| DATED | : August 9, 2011 |
| INVENTOR(S) | : Thomas Zierke et al. |

It is certified that error appears in the above-identified patent and that said Letters Patent is hereby corrected as shown below:

Col. 12, lines 16-27, replace the structure for formula (II) with the following structure:

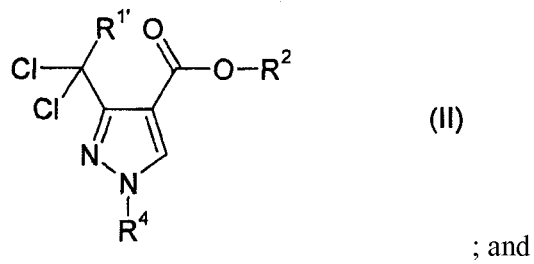

(II)

; and line 42, delete "$R^{1'''}$" and insert therefore --$R^{1'}$--.

Col. 13, line 2, after "$C_1$-$C_6$-alkyl," insert --$C_1$-$C_6$ haloalkyl,--; and lines 2-3, after the group "$C_1$-$C_4$-alkoxyl-$C_1$-$C_4$-alkyl" insert --$C_1$-$C_4$-alkylthio-$C_1$-$C_4$-alkyl,--.

Signed and Sealed this
Fifteenth Day of November, 2011

David J. Kappos
*Director of the United States Patent and Trademark Office*